(12) United States Patent
Matsuo

(10) Patent No.: US 11,258,941 B2
(45) Date of Patent: Feb. 22, 2022

(54) IMAGING SYSTEM ADAPTED TO PERFORM FOCAL SWEEP IMAGING, PROCESSING APPARATUS, AND ENDOSCOPE

(71) Applicant: OLYMPUS CORPORATION, Hachioji (JP)

(72) Inventor: Keigo Matsuo, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/150,568

(22) Filed: Jan. 15, 2021

(65) Prior Publication Data
US 2021/0297599 A1 Sep. 23, 2021

Related U.S. Application Data

(63) Continuation of application No. PCT/JP2018/026692, filed on Jul. 17, 2018.

(51) Int. Cl.
*H04N 5/232* (2006.01)
*H04N 5/225* (2006.01)

(52) U.S. Cl.
CPC ............ *H04N 5/232125* (2018.08); *H04N 2005/2255* (2013.01)

(58) Field of Classification Search
CPC .. H04N 5/232125; H04N 5/232; H04N 5/225; H04N 5/222; H04N 5/217; H04N 2005/2255; H04N 7/18; A61B 1/045
See application file for complete search history.

(56) References Cited

U.S. PATENT DOCUMENTS

| 2013/0010160 A1 | 1/2013 | Kawamura |
| 2013/0307933 A1 | 11/2013 | Znamenskiy et al. |
| 2014/0184883 A1 | 7/2014 | Shimamoto |
| 2018/0007343 A1 | 1/2018 | Send et al. |

FOREIGN PATENT DOCUMENTS

| JP | 2014511590 A | 5/2014 |
| JP | 2018510320 A | 4/2018 |
| WO | 2012105222 A1 | 8/2012 |
| WO | 2013171954 A1 | 11/2013 |

OTHER PUBLICATIONS

International Preliminary Report on Patentability (IPRP) (and English language translation thereof) dated Jan. 19, 2021 issued in International Application No. PCT/JP2018/026692.
International Search Report (ISR) (and English translation thereof) dated Sep. 25, 2018 issued in International Application No. PCT/JP2018/026692.
Kuthirummal, "Flexible Depth of Field Photography", Transactions On Pattern Analysis and Machine Intelligence, 1-15.

*Primary Examiner* — Antoinette T Spinks
(74) *Attorney, Agent, or Firm* — Holtz, Holtz & Volek PC

(57) ABSTRACT

An imaging system includes: an imaging optical system; an imaging element having a two-dimensional pixel array; a drive unit that drives at least one of a focus lens and the imaging element; an IPSF selection unit that selects an IPSF that is used for image generation from among a plurality of IPSFs stored in an IPSF storage unit; and an image generator that generates an image using the selected IPSF.

11 Claims, 13 Drawing Sheets

IMAGING SYSTEM ADAPTED TO PERFORM FOCAL SWEEP IMAGING, PROCESSING APPARATUS, AND ENDOSCOPE

CROSS-REFERENCE TO RELATED APPLICATIONS

This application is based upon and claims the benefit of priority from International Application No. PCT/JP2018/026692, filed on Jul. 7, 2018, the entire contents of which is incorporated herein by reference.

BACKGROUND

1. Field of the Disclosure

The present disclosure relates to an imaging system, a processing apparatus, and an endoscope.

2. Description of the Related Art

The depth of field is one of the characteristics of a lens system in an imaging system and refers to a range where the vicinity of a focusing portion appears to be in focus. The depth of field is determined by (i) an aperture value (F value), (ii) the focal length of the lens, and (iii) the distance from the camera to the subject (imaging distance). Regarding the aperture value of the lens, the smaller the aperture value, the shallower the depth of field (the range that appears to be in focus becomes smaller), and the larger the aperture value, the deeper the depth of field (the range that appears to be in focus becomes larger). An image with a deep depth of field is also called a pan-focus image.

In microscope and endoscopic images, a deep depth of field is often preferred for observation. For example, when imaging a person and a landscape using an imaging apparatus, there is a need to focus on both of them.

In an imaging system, some techniques for extending the depth of field have been proposed. Non-Patent Document 1 discloses a technique relating to focal sweep imaging in which an imaging element is shifted along the optical axis during an exposure period. An image obtained by focal sweep imaging is the integration of images at respective positions during the shifting.

Non-Patent Document 1] Sujit Kuthirummal, Hajime Nagahara, Changyin Zhou, and Shree K. Nayar, "Flexible Depth of Field Photography", IEEE Transactions on Pattern Recognition and Machine Intelligence, Vol. 33, No. 1, pp. 58-71, 2011.01

According to the technique disclosed in Non-Patent Document 1, the relationship between the amount of extension of the depth of field and the resolution is fixed, and the resolution cannot be adjusted according to the imaging distance. Further, sufficient studies have not been made on the restoration of images captured by focal sweep using lighting in the past.

SUMMARY

In this background, one of exemplary purposes of an embodiment of the present disclosure is to provide a technique for acquiring an ideal focal sweep image.

An imaging system according to one embodiment of the present disclosure includes: an imaging optical system; an imaging element having a two-dimensional pixel array; a drive unit that drives at least one of a focus lens and the imaging element; an IPSF selection unit that selects an integrated point spread function that is used for image generation from among a plurality of integrated point spread functions; and an image generator that generates an image using the selected integrated point spread function.

Another embodiment of the present disclosure relates to a processing apparatus. This apparatus includes: an IPSF selection unit that selects an integrated point spread function that is used for image generation from among a plurality of integrated point spread functions; and an image generator that generates an image using the selected integrated point spread function.

Still another embodiment of the present disclosure relates to an endoscope. This endoscope includes: an imaging optical system; an imaging element having a two-dimensional pixel array; and a drive unit that is capable of driving at least one of a focus lens and the imaging element during the exposure period of the imaging element.

Optional combinations of the aforementioned constituting elements, and implementations of the disclosure in the form of methods, apparatuses, systems, or the like may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION

The disclosure will now be described by reference to the preferred embodiments. This does not intend to limit the scope of the present disclosure, but to exemplify the disclosure.

First, an explanation is given of a technique on which the embodiments are based. A technique is known that uses a point spread function (hereinafter also referred to as "PSF") to apply inverse filtering by deconvolution to a blurred image so as to restore the image. PSF is a function representing the response of an optical system to a point light source and is determined according to the optical system of an imaging apparatus.

Figure 1:
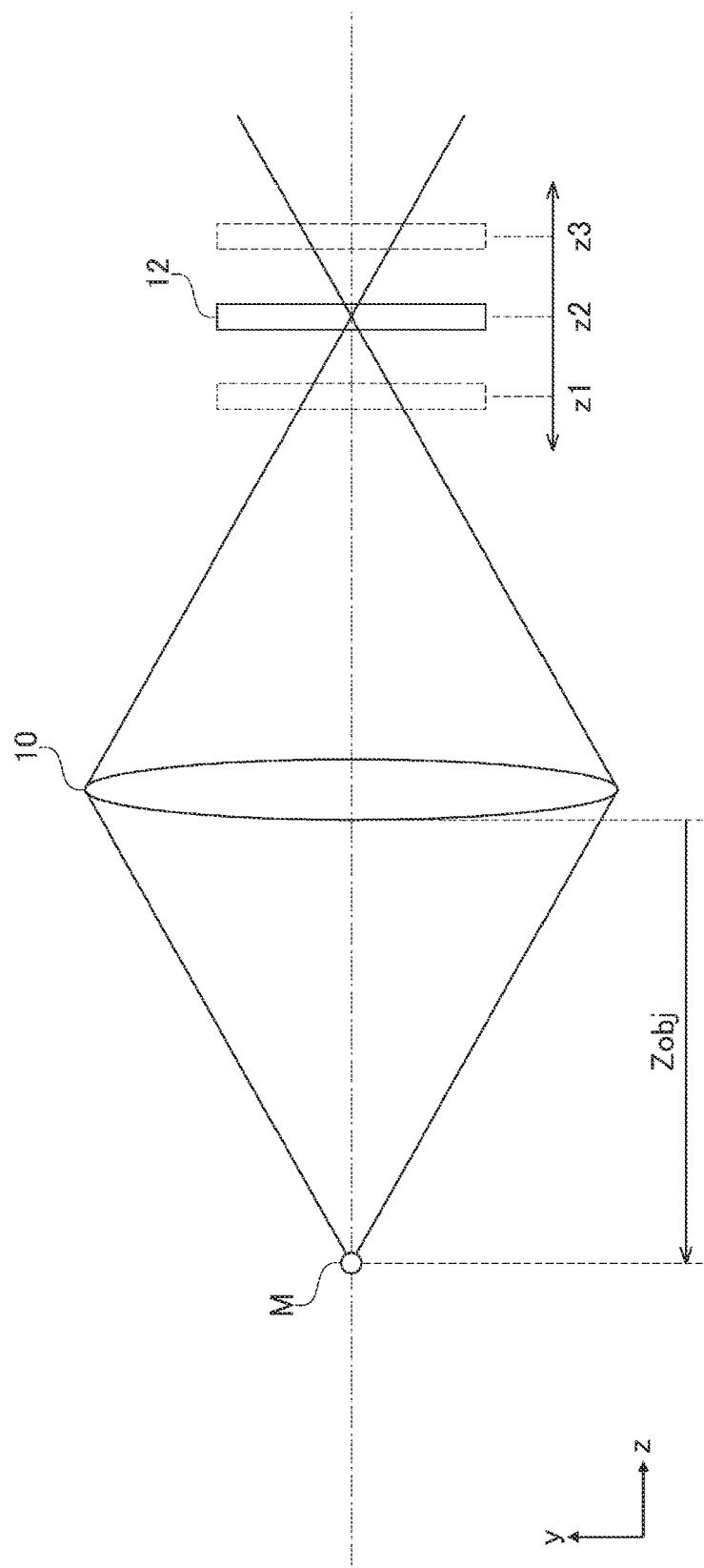
FIG. 1 is a diagram for explaining focal sweep imaging.

FIG. 1 is a diagram for explaining focal sweep imaging. A focal sweep imaging system captures a focal sweep image in which multiple focal points are superimposed by moving at least one of a focus lens 10 and an imaging element 12 included in the imaging optical system along the optical axis (Z axis) during an exposure period. FIG. 1 shows a state in which the imaging element 12 is moved in the optical axis direction so as to perform focal sweep imaging of an object point M, which is a point light source. The distance (imaging distance) from a lens system to the object point M is Zobj, and when the imaging element 12 is at a position z2 on the Z axis, the object point M passes through the focus lens 10, and an image is formed at an imaging surface of the imaging element 12.

Figure 2:
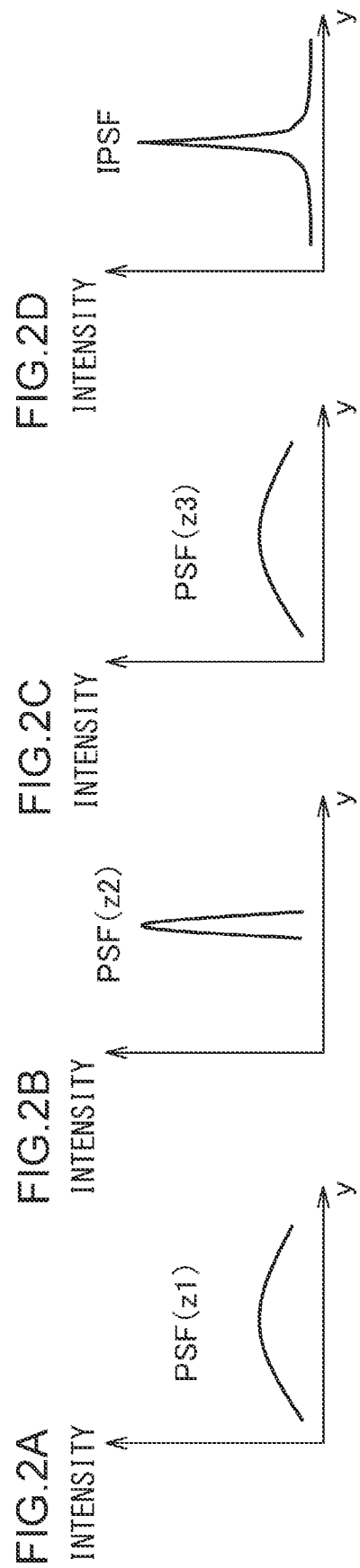
FIGS. 2A to 2C are diagrams showing an example of PSF.
FIG. 2D is a diagram showing an example of ISPF.

FIG. 2A shows an example of the PSF when the imaging element 12 is at a position z1. FIG. 2B shows the PSF when the imaging element 12 is at the position z2. FIG. 2C shows the PSF when the imaging element 12 is at position z3. In FIGS. 2A to 2C, the PSF is expressed in one dimension for easy understanding. However, the PSF is actually a two-dimensional function. In the example in FIG. 1, since the object point M is in focus when the imaging element 12 is at the position z2, the PSF in FIG. 2B has a high peak intensity.

An image captured by focal sweep imaging is restored using an integrated point spread function (hereinafter, also referred to as "IPSF") where a PSF at each position of the imaging element 12 moved during the exposure period is integrated. The restored image is an image with an extended depth of field. FIG. 2D shows an example of IPSF in which a plurality of PSFs are integrated. The IPSF is acquired by calculation or by actually performing focal sweep imaging of a point light source.

It is known that IPSF does not depend on the position of an object point as long as the imaging conditions are the same. The imaging conditions include the driving speed of at least one of the focus lens 10 and the imaging element 12. By imaging the subject under the same imaging conditions as the imaging conditions at the time of acquiring IPSF, the imaging system can acquire an image with an extended depth of field using the IPSF.

Figure 3:
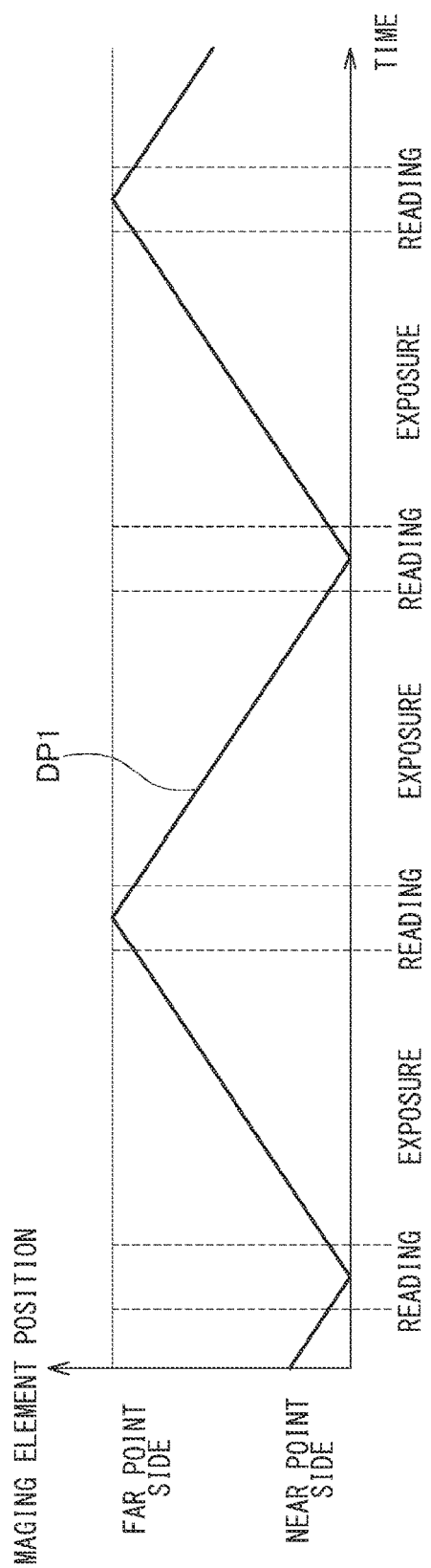
FIG. 3 is a diagram showing an example of a drive pattern of an imaging element.

FIG. 3 shows a drive pattern DP1 of the imaging element 12. The horizontal axis of FIG. 3 indicates time, and the vertical axis indicates the position of the imaging element 12. According to the drive pattern DP1, the imaging element 12 is moved at a constant speed along the optical axis between the near point (near end) position and the far point (far end) position of the depth of field. The near point position is the position of the imaging element 12 at which the subject at the near end of the extended depth of field is in focus, and the far point position is the position of the imaging element 12 at which the subject at the far end of the extended depth of field is in focus. As described above, the focal sweep image is also captured by moving the focus lens 10 in the optical axis direction.

On the time axis, an "exposure" period in which the imaging element 12 is exposed so as to generate an image signal and a "read" period in which the image signal is read from the imaging element 12 are shown. By continuously moving the imaging element 12 at a constant speed, the amount of image information at each position in a moving section of the imaging element 12 is uniformly integrated.

Figure 4:
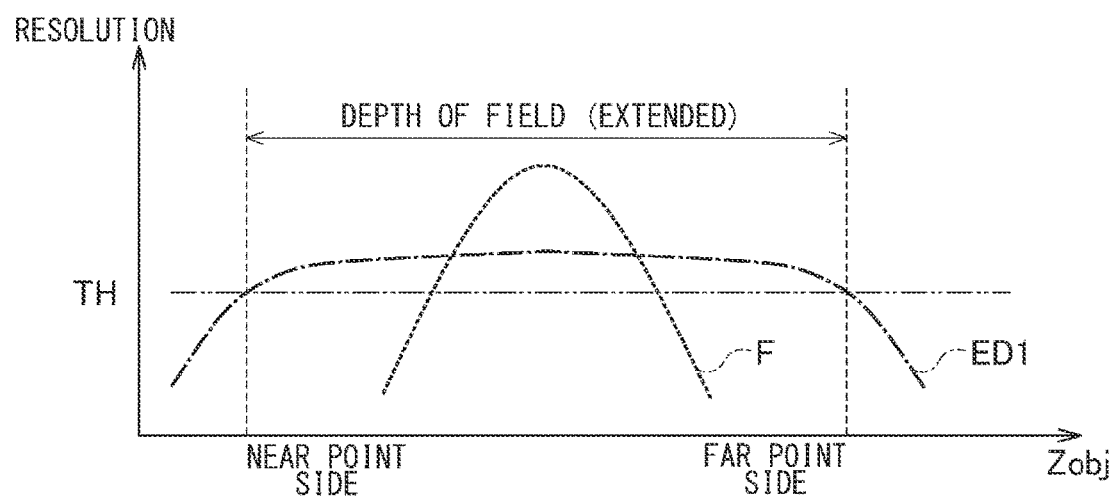
FIG. 4 is a diagram showing an example of the depth of field.

FIG. 4 shows the depth of field when the imaging element 12 is driven by the drive pattern DP1 so as to restore the image. The horizontal axis in FIG. 4 indicates the distance from the imaging apparatus to the object point (imaging distance), and the vertical axis indicates the resolution. A threshold value TH represents resolution at which a person determines that the focusing is achieved, and the range of the imaging distance that exceeds the threshold value TH represents the depth of field (focusing range).

A resolution characteristic F indicates the relationship between the resolution and the imaging distance in normal focused imaging. A resolution characteristic ED1 indicates the relationship between the resolution and the imaging distance in focal sweep imaging using the drive pattern DP1 shown in FIG. 3. Comparing the resolution characteristic F and the resolution characteristic ED1, it is shown that the depth of field is extended by the focal sweep imaging at a uniform resolution.

Extension of the depth of field is particularly suitable for images for observation purposes. For example, by providing an endoscope with a focal sweep imaging function, it is possible to provide a doctor with an image with an extended depth of field and support the observation of an internal body image.

An object to be observed in an endoscopic examination is the inside of the patient's digestive tract. Therefore, in an endoscopic examination, there is a need to observe a part located at a specific imaging distance in more detail according to the type and purpose of the examination. Therefore, it is desired to provide an internal body image in which the resolution at a specific imaging distance is higher than the resolution at another imaging distance.

Hereinafter, the present disclosure will be described based on a preferred embodiment with reference to the figures. Further, the embodiments do not limit the disclosure and are shown for illustrative purposes, and not all the features described in the embodiments and combinations thereof are necessarily essential to the disclosure. The vertical and horizontal axes of the graphs referred to in the present specification are scaled up or down as appropriate to facilitate understanding, and the graphs and waveforms shown are also simplified for easy understanding or are exaggerated or emphasized.

Figure 5:
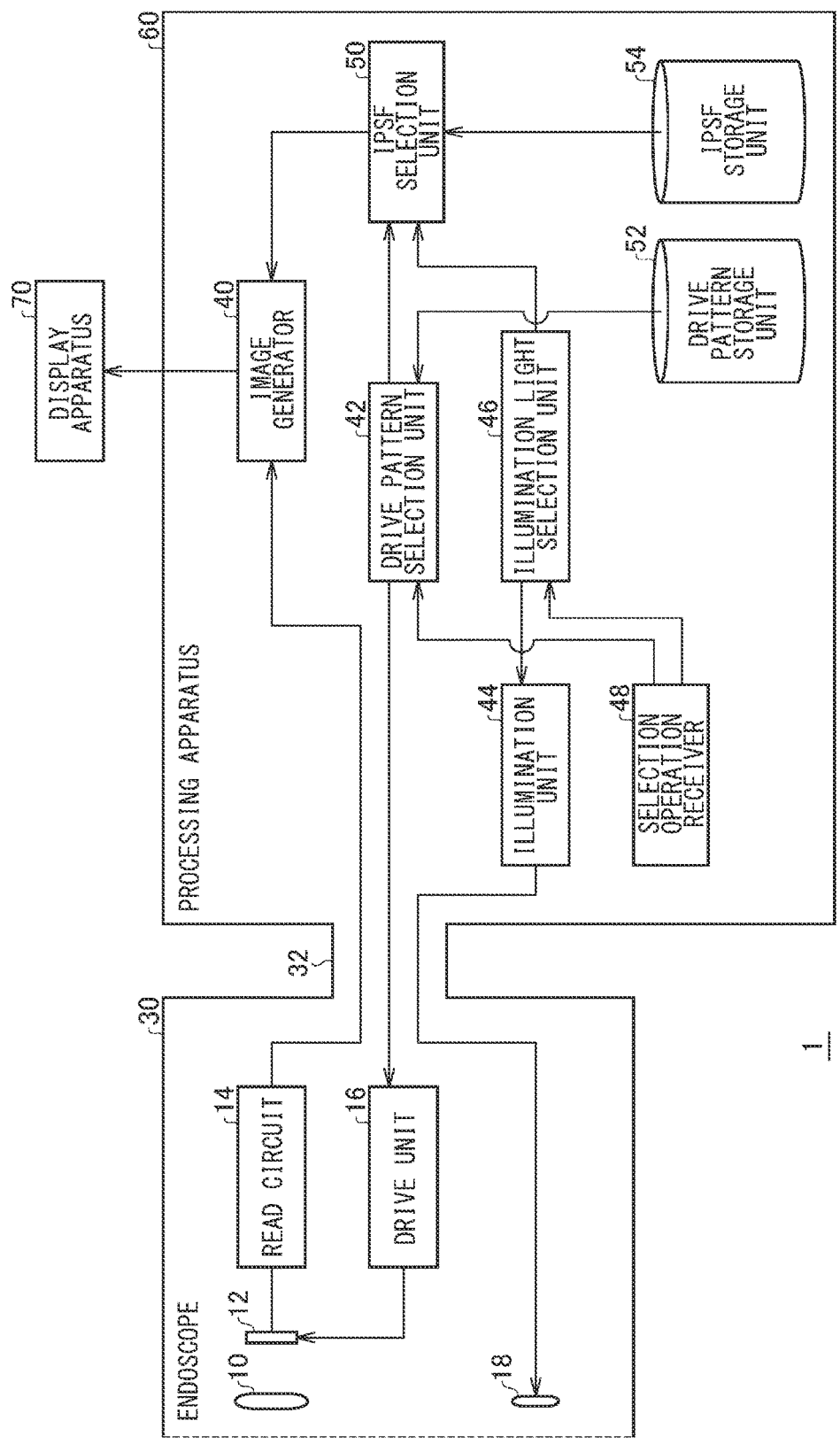
FIG. 5 is a diagram showing the configuration of an imaging system according to an embodiment.

FIG. 5 shows the configuration of an imaging system 1 according to an embodiment. The imaging system 1 includes an endoscope 30 serving as an imaging apparatus, a processing apparatus 60, and a display apparatus 70. The processing apparatus 60 includes a processor including hardware. Before the start of an endoscopic examination, a connecting part 32 of the endoscope 30 is connected to the processing apparatus 60. During the examination, the endoscope 30 is inserted into the patient's body, and the processing apparatus 60 restores an internal body image captured by the endoscope 30 through focal sweep imaging at a predetermined cycle using the IPSF and displays the restored internal body image on the display apparatus 70. The doctor observes the internal body image displayed on the display apparatus 70 and checks whether there are lesions.

The endoscope 30 includes an imaging optical system including a focus lens 10, an imaging element 12, a read circuit 14, a drive unit 16, and an illumination lens 18. The focus lens 10 and the illumination lens 18 are provided at the tip of the endoscope 30. The illumination lens 18 emits illumination light guided by an optical fiber from an illumination unit 44 provided in the processing apparatus 60 into the patient's body.

The imaging element 12 is a charge coupled device (CCD) image sensor, a complementary metal oxide semiconductor (CMOS) image sensor, or the like and has a two-dimensional pixel array in which a plurality of pixels are arranged in a matrix. Along with another imaging lens (not shown), the focus lens 10 forms an imaging optical system that forms an image of a subject on an imaging surface of the imaging element 12. The read circuit 14 reads an image signal from the imaging element 12 at a predetermined cycle.

The drive unit 16 has an actuator capable of driving at least one of the focus lens 10 and the imaging element 12 during the exposure period of the imaging element 12. By driving at least one of the focus lens 10 and the imaging element 12 during the exposure period, focal sweep imaging in the endoscope 30 is realized. In the embodiment, the drive unit 16 drives the imaging element 12.

Alternatively, the drive unit 16 may drive the focus lens 10 or drive both the focus lens 10 and the imaging element 12. In the embodiment, the imaging optical system of the endoscope 30 includes the focus lens 10. However, when the imaging optical system does not include the focus lens 10, the drive unit 16 drives the imaging element 12 so as to realize focal sweep imaging.

The processing apparatus 60 includes an image generator 40, a drive pattern selection unit 42, an illumination unit 44, an illumination light selection unit 46, a selection operation receiver 48, an IPSF selection unit 50, a drive pattern storage unit 52, and an IPSF storage unit 54. The processing apparatus 60 includes a processor including hardware. The functions of the processing apparatus 60 are implemented by any CPU, a memory or a program loaded into the memory. Configurations are implemented by the cooperation of hardware components. Thus, a person skilled in the art should appreciate that there are many ways of accomplishing these functional blocks in various forms in accordance with the components of hardware only, software only, or the combination of both.

The illumination unit 44 has a light source that emits light having at least one wavelength so as to illuminate the subject. In a normal endoscopic examination, white light is used as the illumination light. However, in a special endoscopic examination, light of a specific wavelength is used as the illumination light. The illumination light selection unit 46 selects the wavelength of light emitted from the illumination unit 44 according to an observation mode in an endoscope examination, and the illumination unit 44 emits illumination light of the selected wavelength into the body.

The selection operation receiver 48 receives a selection operation from a doctor. During the examination, the doctor operates an operation unit such as a switch or a button provided on the endoscope 30 as necessary so as to select an observation mode. The operation unit may be provided in the processing apparatus 60, and a nurse may select the observation mode according to an instruction from the doctor. Upon receiving a selection operation for an observation mode, the selection operation receiver 48 supplies the selection operation for the observation mode to the illumination light selection unit 46, and the illumination light selection unit 46 selects the wavelength of light emitted from the illumination unit 44 according to the observation mode.

Further, during the examination, the doctor operates the operation unit provided on the endoscope 30 so as to select a depth of field extension mode. Upon receiving the selection operation for the depth of field extension mode, the selection operation receiver 48 supplies the selection operation for the depth of field extension mode to the drive pattern selection unit 42.

The drive pattern storage unit 52 stores a plurality of drive patterns of the imaging element 12. A drive pattern is a periodic waveform in which the speed at which the imaging element 12 is driven along the optical axis within a movement range between a near point position and a far point position is defined according to the position in the movement range. The cycle of the drive pattern may be an integral multiple of a field cycle including an exposure period and a read period. In the embodiment, a drive pattern in which the imaging element 12 moves to the near point position and the far point position during the reading period of the imaging element 12 is adopted. However, the present disclosure is not limited to this. Each of the plurality of drive patterns causes the drive speed to change at least once during the exposure period of the imaging element 12.

The IPSF storage unit 54 stores an IPSF that corresponds to a drive pattern stored in the drive pattern storage unit 52. The IPSF is acquired for each drive pattern by calculation or by actually performing focal sweep imaging of a point light source and is stored in the IPSF storage unit 54. The IPSF selection unit 50 selects the IPSF to be used for image generation from among the plurality of IPSFs stored in the IPSF storage unit 54. The image generator 40 uses the IPSF selected by the IPSF selection unit 50 so as to generate an image with an extended depth of field.

In the imaging system 1 according to the embodiment, the drive speed of the imaging element 12 during the exposure period is changed according to the drive pattern such that the amount of image information acquired at each position of the moving section of the imaging element 12 is biased. Thereby, the resolution of a subject at a specific imaging distance is increased. More specifically, by slowing down the driving speed at a position corresponding to an imaging distance at which the resolution is desired to be increased, the amount of image information acquired by the imaging element 12 is increased, and the resolution of a subject at the imaging distance is enhanced.

First Exemplary Embodiment

Figure 6:
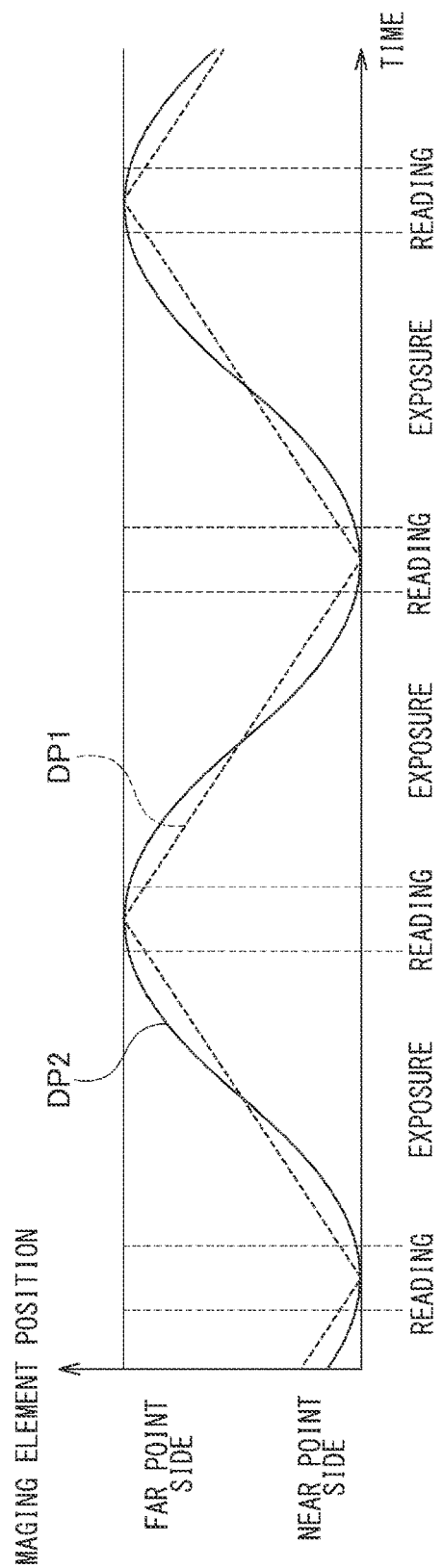
FIG. 6 is a diagram showing a drive pattern of an imaging element in the first exemplary embodiment.

FIG. 6 shows a drive pattern DP2 of the imaging element 12 in the first exemplary embodiment. The horizontal axis of FIG. 6 indicates time, and the vertical axis indicates the position of the imaging element 12. Compared with the drive pattern DP1 having a triangular waveform, the drive speed of the imaging element 12 in the drive pattern DP2 is set to be slow at a position on the near point side and a position on the far point side of the depth of field and to be fast at a position near the center of the depth of field. Therefore, during the exposure period, the imaging element 12 moves slowly at a position on the near point side and a position on the far point side as compared with the center position and acquires more image information on the near point side and the far point side. The drive pattern DP2 may include the same speed change pattern on the near point side and on the far point side. The drive pattern DP2 may be typically expressed by a sinusoidal waveform or may be expressed by another waveform. Since the drive unit 16 switches the drive direction of the imaging element 12 at a near point and a far point, there is an advantage that the drive load at the time of the switching can be reduced according to the drive pattern DP2 in which the drive speed at the near point and the far point is slow.

When the doctor desires to observe images near both ends of the depth of field in detail, the doctor operates the operation unit of the endoscope 30 so as to select a depth of field extension mode that uses the drive pattern DP2. Upon receiving the selection operation for the depth of field extension mode, the selection operation receiver 48 supplies selection operation information to the drive pattern selection unit 42. The drive pattern selection unit 42 selects the drive pattern DP2 from among the plurality of drive patterns stored in the drive pattern storage unit 52 and supplies the drive pattern DP2 to the drive unit 16. Thereby, the drive unit 16 drives the imaging element 12 using the drive pattern DP2. The IPSF selection unit 50 selects the IPSF that corresponds to the selected drive pattern DP2 from among the plurality of IPSFs stored in the IPSF storage unit 54 and supplies the IPSF to the image generator 40. Using the IPSF selected by the IPSF selection unit 50, the image generator 40 restores an image with an extended depth of field from an image signal read from the read circuit 14 at a predetermined cycle and displays the image on the display apparatus 70.

Figure 7:
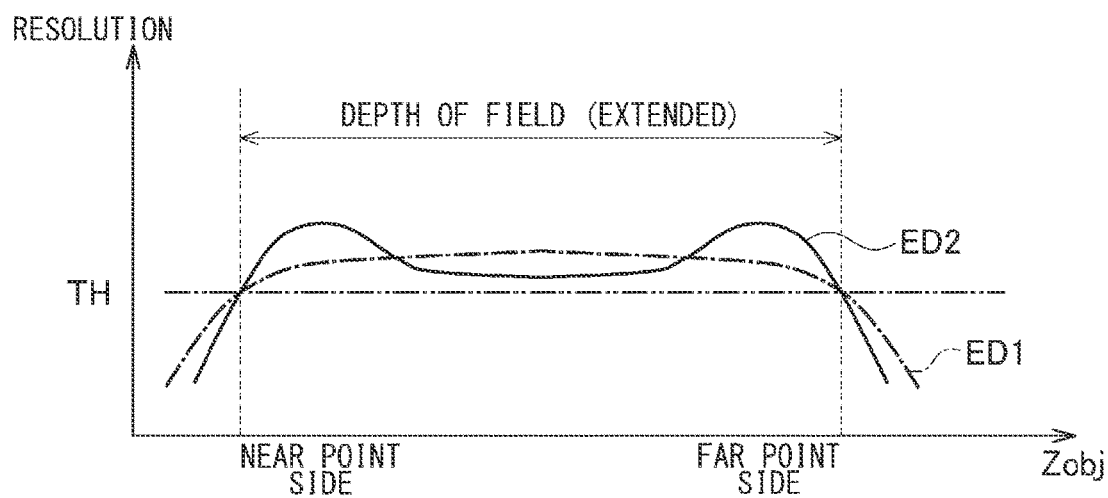
FIG. 7 is a diagram showing an example of the depth of field.

FIG. 7 shows the depth of field when the imaging element 12 is driven by the drive pattern DP2 so as to restore the image. The horizontal axis of FIG. 7 shows the imaging distance, and the vertical axis shows the resolution. A resolution characteristic ED2 indicates the relationship between the resolution and the imaging distance in focal sweep imaging using the drive pattern DP2 shown in FIG. 6. Compared with the resolution characteristic ED1 by the drive pattern DP1, the resolution is shown to be increased at positions on the near point side and the far point side of the depth of field in the resolution characteristic ED2.

In the first exemplary embodiment, by using the drive pattern DP2 that slows down the drive speed on the near point side and the far point side of the depth of field, the resolution near both ends of the depth of field can be improved. In compensation for an increase in the resolution on the near point side and the far point side, the resolution on the center side decreases. The doctor selects the depth of field extension mode using the drive pattern DP2 when the doctor desires to observe both a near part and a far part in the gastrointestinal tract in detail at the same time.

Second Exemplary Embodiment

Figure 8:
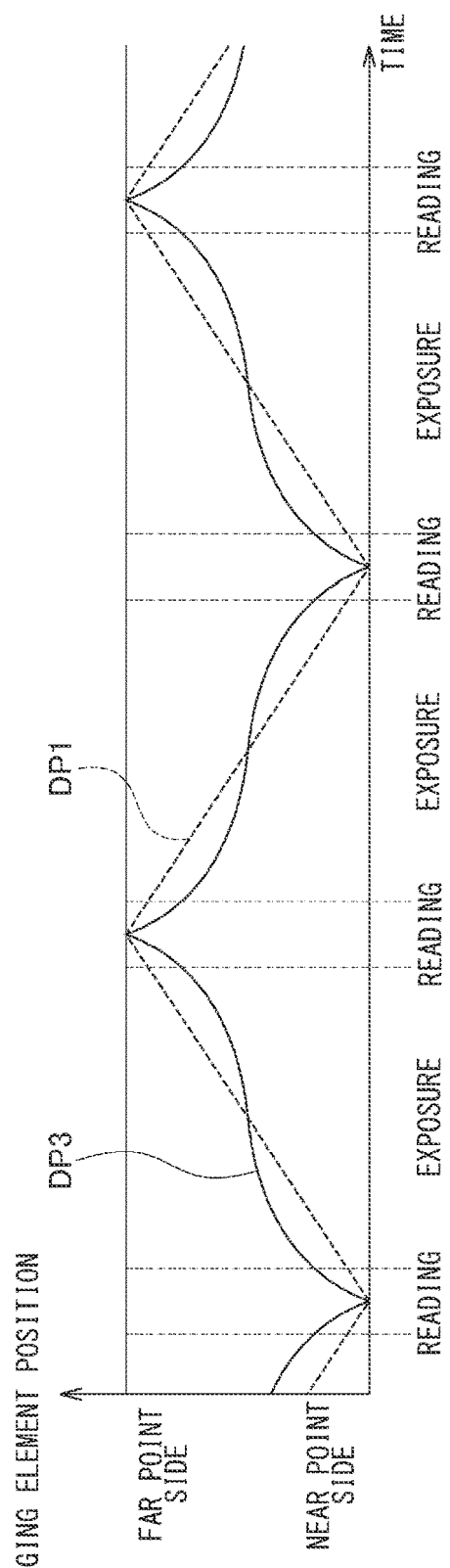
FIG. 8 is a diagram showing a drive pattern of an imaging element in the second exemplary embodiment.

FIG. 8 shows a drive pattern DP3 of an imaging element 12 in the second exemplary embodiment. The horizontal axis of FIG. 8 indicates time, and the vertical axis indicates the position of the imaging element 12. Compared with the drive pattern DP1 having a triangular waveform, the drive speed of the imaging element 12 in the drive pattern DP3 is set to be fast at a position on the near point side and a position on the far point side of the depth of field and to be slow at a position near the center of the depth of field. Therefore, during the exposure period, the imaging element 12 moves slowly around the center position as compared with a position on the near point side and a position on the far point side and acquires more image information around the center position. The drive pattern DP3 may include the same speed change pattern on the near point side and on the far point side.

When the doctor desires to observe an image near the center of the depth of field in detail, the doctor operates the operation unit of the endoscope 30 so as to select a depth of field extension mode that uses the drive pattern DP3. The drive pattern selection unit 42 selects the drive pattern DP3 from among the plurality of drive patterns stored in the drive pattern storage unit 52 and supplies the drive pattern DP3 to the drive unit 16. Thereby, the drive unit 16 drives the imaging element 12 using the drive pattern DP3. The IPSF selection unit 50 selects the IPSF that corresponds to the selected drive pattern DP3 from among the plurality of IPSFs stored in the IPSF storage unit 54 and supplies the IPSF to the image generator 40. Using the IPSF selected by the IPSF selection unit 50, the image generator 40 restores an image with an extended depth of field from an image signal read from the read circuit 14 at a predetermined cycle and displays the image on the display apparatus 70.

Figure 9:
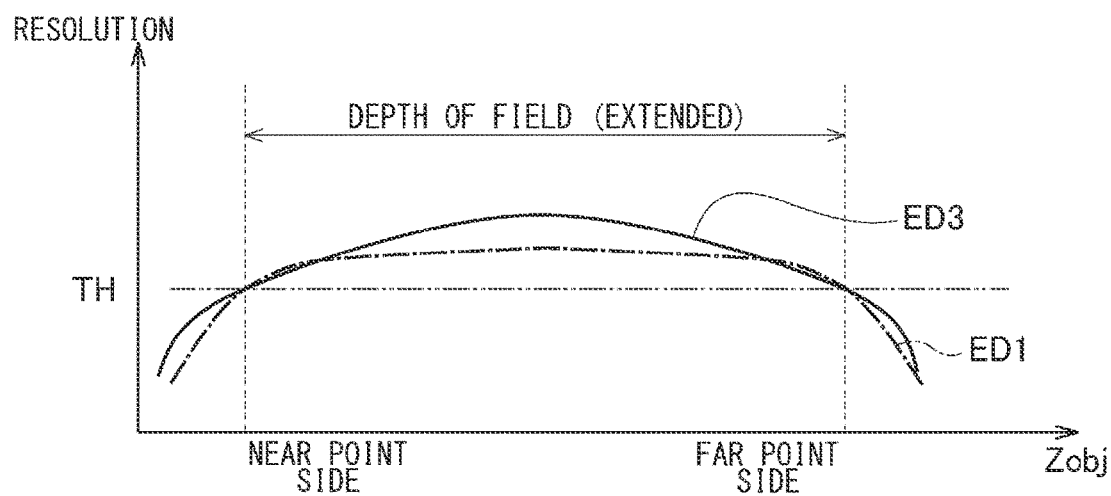
FIG. 9 is a diagram showing an example of the depth of field.

FIG. 9 shows the depth of field when the imaging element 12 is driven by the drive pattern DP3 so as to restore the image. The horizontal axis of FIG. 9 shows the imaging distance, and the vertical axis shows the resolution. A resolution characteristic ED3 indicates the relationship between the resolution and the imaging distance in focal sweep imaging using the drive pattern DP3 shown in FIG. 8. Compared with the resolution characteristic ED1 by the drive pattern DP1, the resolution is shown to be increased at a position on the center side of the depth of field in the resolution characteristic ED3.

In the second exemplary embodiment, by using the drive pattern DP3 that slows down the drive speed at the center of the depth of field, the resolution near the center of the depth of field can be improved. In compensation for an increase in the resolution near the center, the resolution on both end sides decreases. The doctor selects the depth of field extension mode using the drive pattern DP3 when the doctor desires to observe a part near the center of the depth of filed in the gastrointestinal tract in detail.

Third Embodiment

Figure 10:
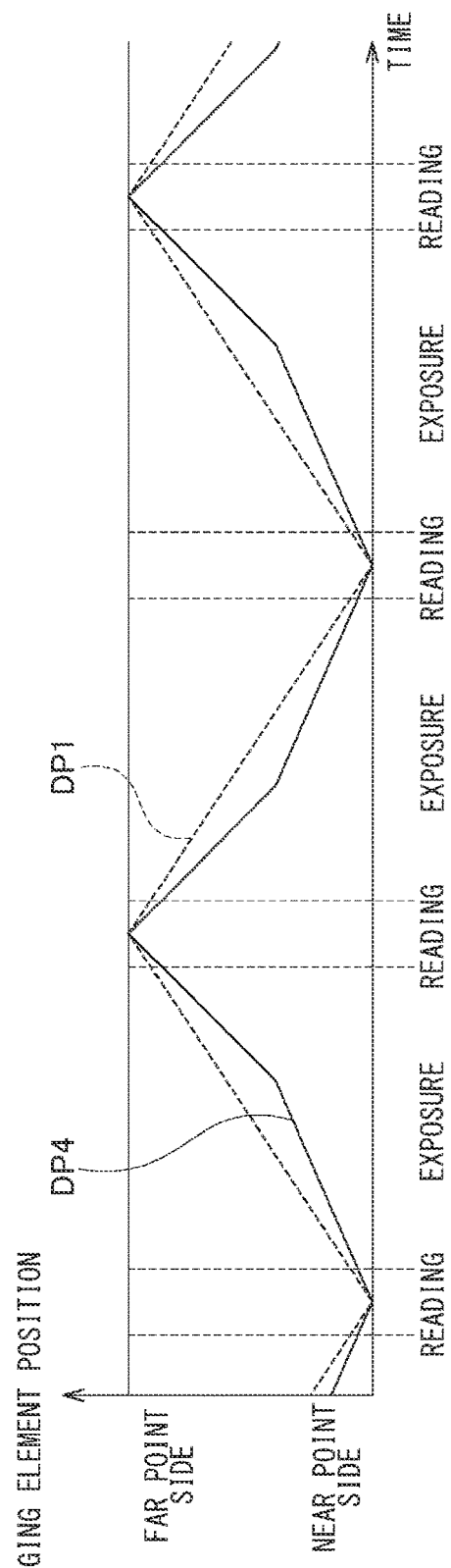
FIG. 10 is a diagram showing a drive pattern of an imaging element in the third exemplary embodiment.

FIG. 10 shows a drive pattern DP4 of an imaging element 12 in the third exemplary embodiment. The horizontal axis of FIG. 10 indicates time, and the vertical axis indicates the position of the imaging element 12. Compared with the drive pattern DP1 having a triangular waveform, the drive speed of the imaging element 12 in the drive pattern DP4 is set to be fast at a position on the far point side of the depth of field and to be slow at a position on the near point side of the depth of field. Therefore, during the exposure period, the imaging element 12 moves slowly at a position on the near point side as compared with a position on the far point side and acquires more image information on the near point side. The drive pattern DP4 may be expressed by a curved line instead of a polygonal line.

When the doctor desires to observe an image on the near point side of the depth of field in detail, the doctor operates the operation unit of the endoscope 30 so as to select a depth of field extension mode that uses the drive pattern DP4. The drive pattern selection unit 42 selects the drive pattern DP4 from among the plurality of drive patterns stored in the drive pattern storage unit 52 and supplies the drive pattern DP4 to the drive unit 16. Thereby, the drive unit 16 drives the imaging element 12 using the drive pattern DP4. The IPSF selection unit 50 selects the IPSF that corresponds to the selected drive pattern DP4 from among the plurality of IPSFs stored in the IPSF storage unit 54 and supplies the IPSF to the image generator 40. Using the IPSF selected by the IPSF selection unit 50, the image generator 40 restores an image with an extended depth of field from an image signal read from the read circuit 14 at a predetermined cycle and displays the image on the display apparatus 70.

Figure 11:
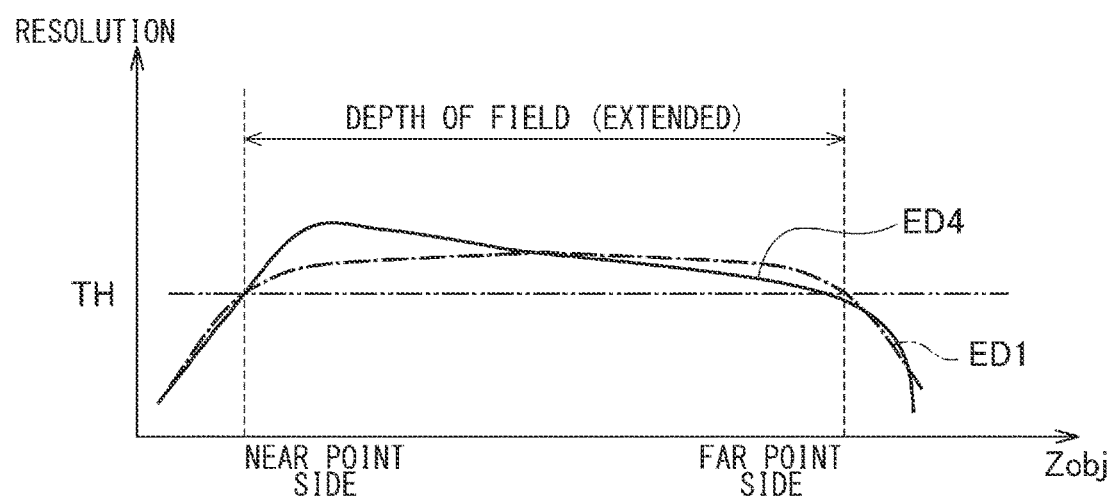
FIG. 11 is a diagram showing an example of the depth of field.

FIG. 11 shows the depth of field when the imaging element 12 is driven by the drive pattern DP4 so as to restore the image. The horizontal axis of FIG. 11 shows the imaging distance, and the vertical axis shows the resolution. A resolution characteristic ED4 indicates the relationship between the resolution and the imaging distance in focal sweep imaging using the drive pattern DP4 shown in FIG.

10. Compared with the resolution characteristic ED1 by the drive pattern DP1, the resolution is shown to be increased at a position on the near point side of the depth of field in the resolution characteristic ED4.

In the third exemplary embodiment, by using the drive pattern DP4 that slows down the drive speed on the near point side of the depth of field, the resolution on the near point side of the depth of field can be improved. In compensation for an increase in the resolution on the near point side, the resolution on the far point side decreases. The doctor selects the depth of field extension mode using the drive pattern DP4 when the doctor desires to observe a part on the near point side of the depth of filed in the gastrointestinal tract in detail.

Fourth Embodiment

Figure 12:
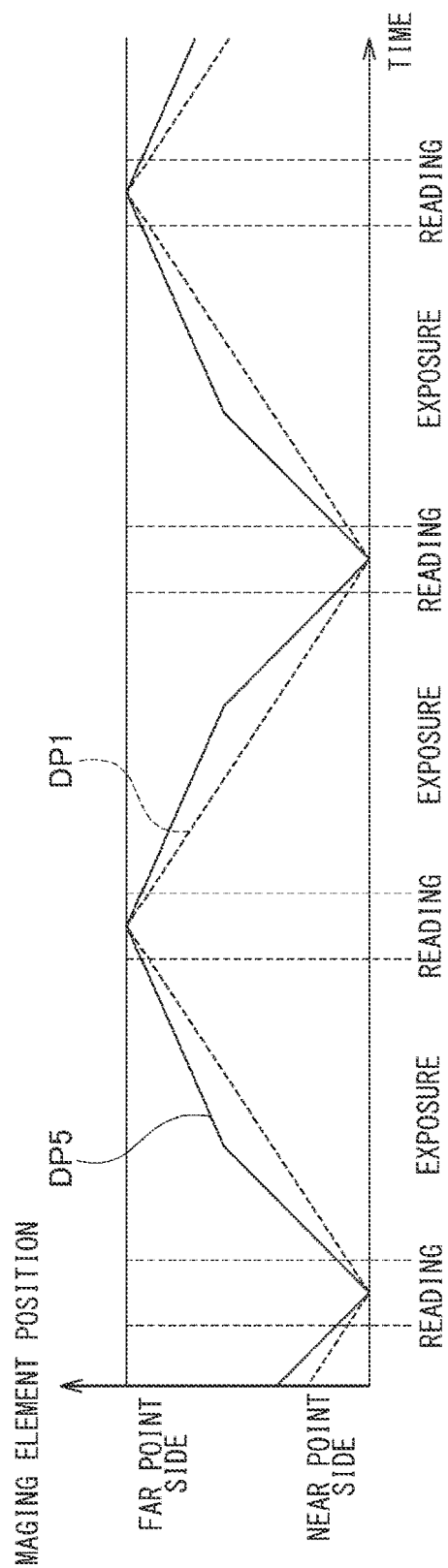
FIG. 12 is a diagram showing a drive pattern of an imaging element in the fourth exemplary embodiment.

FIG. 12 shows a drive pattern DP5 of the imaging element 12 in the fourth exemplary embodiment. The horizontal axis of FIG. 12 indicates time, and the vertical axis indicates the position of the imaging element 12. Compared with the drive pattern DP1 having a triangular waveform, the drive speed of the imaging element 12 in the drive pattern DP5 is set to be fast at a position on the near point side of the depth of field and to be slow at a position on the far point side of the depth of field. Therefore, during the exposure period, the imaging element 12 moves slowly at a position on the far point side as compared with a position on the near point side and acquires more image information on the far point side. The drive pattern DP5 may be expressed by a curved line instead of a polygonal line.

When the doctor desires to observe an image on the far point side of the depth of field in detail, the doctor operates the operation unit of the endoscope 30 so as to select a depth of field extension mode that uses the drive pattern DP5. The drive pattern selection unit 42 selects the drive pattern DP5 from among the plurality of drive patterns stored in the drive pattern storage unit 52 and supplies the drive pattern DP5 to the drive unit 16. Thereby, the drive unit 16 drives the imaging element 12 using the drive pattern DP5. The IPSF selection unit 50 selects the IPSF that corresponds to the selected drive pattern DP5 from among the plurality of IPSFs stored in the IPSF storage unit 54 and supplies the IPSF to the image generator 40. Using the IPSF selected by the IPSF selection unit 50, the image generator 40 restores an image with an extended depth of field from an image signal read from the read circuit 14 at a predetermined cycle and displays the image on the display apparatus 70.

Figure 13:
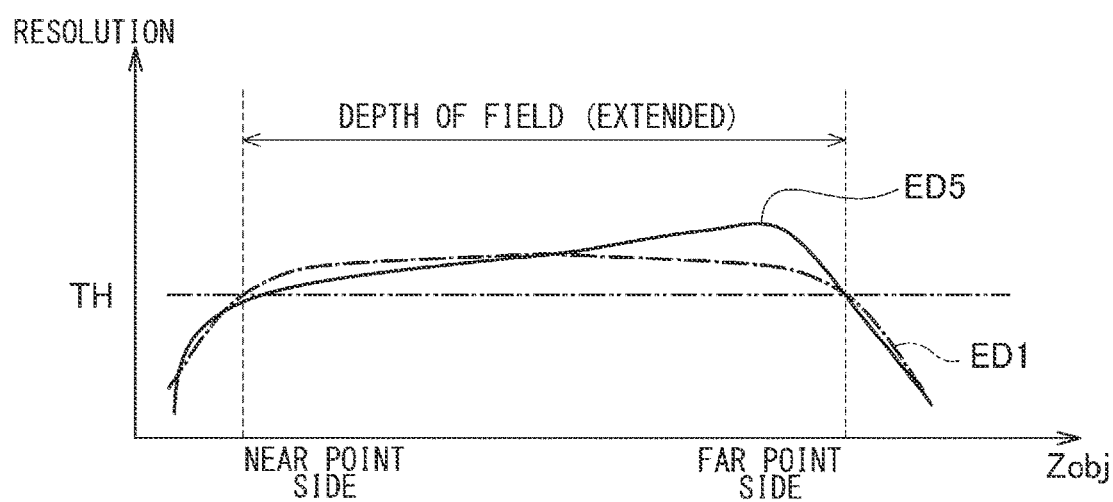
FIG. 13 is a diagram showing an example of the depth of field.

FIG. 13 shows the depth of field when the imaging element 12 is driven by the drive pattern DP5 so as to restore the image. The horizontal axis of FIG. 13 shows the imaging distance, and the vertical axis shows the resolution. A resolution characteristic ED5 indicates the relationship between the resolution and the imaging distance in focal sweep imaging using the drive pattern DP5 shown in FIG. 12. Compared with the resolution characteristic ED1 by the drive pattern DP1, the resolution is shown to be increased at a position on the far point side of the depth of field in the resolution characteristic ED5.

In the fourth exemplary embodiment, by using the drive pattern DP5 that slows down the drive speed on the far point side of the depth of field, the resolution on the far point side of the depth of field can be improved. In compensation for an increase in the resolution on the far point side, the resolution on the near point side decreases. The doctor selects the depth of field extension mode using the drive pattern DP5 when the doctor desires to observe a part on the far point side of the depth of filed in the gastrointestinal tract in detail.

Fifth Embodiment

In the first to fourth exemplary embodiments, the IPSF selection unit 50 selects an IPSF that corresponds to a drive pattern selected by the drive pattern selection unit 42, and the image generator 40 generates a restored image using the selected IPSF. In the fifth exemplary embodiment, the image generator 40 generates a restored image with a depth of field extended for each color filter by using an IPSF in which the characteristics of the color filter in the imaging element 12 are taken into consideration.

As described above, in a normal endoscopic examination, white light is used as the illumination light. However, in a special endoscopic examination, light of a specific wavelength is used as the illumination light. For example, in narrow band imaging (NGI), special illumination light (green wavelength and blue wavelength) that is easily absorbed by hemoglobin in the blood is used to facilitate the observation of blood vessels in the mucous membrane in a more clear manner. During an examination, when the doctor operates the operation unit provided on the endoscope 30 so as to select an observation mode, the selection operation receiver 48 receives the selection operation for the observation mode and supplies the observation mode to the illumination light selection unit 46. The illumination light selection unit 46 selects the wavelength of light emitted from the illumination unit 44 according to the observation mode.

The IPSF storage unit 54 stores an IPSF that corresponds to the wavelength of the light emitted from the illumination unit 44 for each color filter of the imaging element 12. For each illumination light emitted from the illumination unit 44, the IPSF is acquired for each color filter by calculation or by actually performing focal sweep imaging of a point light source and is stored in the IPSF storage unit 54. In the case of examples of white light and special light, the IPSF obtained when white light having red, green, and blue wavelengths is emitted, and the ISPF obtained when special light having green and blue wavelengths is emitted are each acquired for each color filter and stored in the IPSF storage unit 54. Further, if there is special light used in another observation mode, the IPSF that corresponds to the wavelength of the special light is also stored in the IPSF storage unit 54.

The IPSF selection unit 50 selects the IPSF that corresponds to the wavelength of the light emitted from the illumination unit 44 from among the plurality of IPSFs stored in the IPSF storage unit 54 for each color filter. The image generator 40 uses the IPSF selected by the IPSF selection unit 50 so as to generate an image with an extended depth of field.

In an endoscopic examination, the illumination unit 44 emits light having two or more wavelengths so as to illuminate the subject. The IPSF selection unit 50 selects IPSFs that correspond to the two or more wavelengths of the light emitted from the illumination unit 44. In the fifth exemplary embodiment, by preparing an IPSF that corresponds to the wavelength of the illumination light from the illumination unit 44, it is possible to generate an image in which the depth of field is suitably extended according to the observation mode of the endoscopic examination.

Described above is an explanation on the present disclosure based on the embodiments and the exemplary embodiments. These embodiments are intended to be illustrative only, and it will be obvious to those skilled in the art that various modifications to constituting elements and processes could be developed and that such modifications are also within the scope of the present disclosure.

In the embodiment, it is described that the drive unit 16 drives the imaging element 12 in order to realize focal sweep imaging. Alternatively, the drive unit 16 may drive the focus lens 10 or drive both the focus lens 10 and the imaging element 12.

Further, in the embodiment, the endoscope 30 is shown as an example of an imaging apparatus. However, the imaging apparatus is not limited to the endoscope 30 and may be a microscope. The imaging apparatus may be a digital camera or a digital video camera or may be an electronic device having an imaging function such as a smartphone, a tablet terminal, or a laptop computer. The imaging optical system of the imaging apparatus does not have to have the focus lens 10.

What is claimed is:

1. An imaging system comprising:
   an imaging optical system;
   an imaging element having a two-dimensional pixel array;
   a drive unit that drives at least one of a focus lens included in the imaging optical system and the imaging element;
   an illumination unit that emits light having at least one wavelength so as to illuminate a subject; and
   a processor comprising hardware,
   wherein the processor is configured to:
      select an integrated point spread function that is used for image generation from among a plurality of integrated point spread functions; and
      generate an image using the selected integrated point spread function, and
   wherein the processor is configured to select, as the selected integrated point spread function, an integrated point spread function from among the plurality of integrated point spread functions that corresponds to the wavelength of the light emitted from the illumination unit.

2. The imaging system according to claim 1, wherein the processor is configured to:
   select a drive pattern which the drive unit uses during an exposure period of the imaging element from among a plurality of drive patterns; and
   select, as the integrated point spread function, an integrated point spread function from among the plurality of integrated point spread functions that corresponds to the selected drive pattern.

3. The imaging system according to claim 2, wherein the selected drive pattern causes a drive speed to change during the exposure period of the imaging element.

4. The imaging system according to claim 1, wherein the processor is configured to:
   select the wavelength of the light emitted from the illumination unit; and
   select, as the integrated point spread function, an integrated point spread function from among the plurality of integrated point spread functions that corresponds to the selected wavelength of the light.

5. The imaging system according to claim 1, wherein:
   the illumination unit emits light having at least two wavelengths so as to illuminate the subject, and
   the processor is configured to select integrated point spread functions from among the plurality of integrated point spread functions that correspond to the at least two or more wavelengths of the light emitted from the illumination unit.

6. A processing apparatus comprising:
   a processor comprising hardware,
   wherein the processor is configured to:
      select an integrated point spread function that is used for image generation from among a plurality of integrated point spread functions; and
      generate an image using the selected integrated point spread function, and
   wherein the processor is configured to select, as the integrated point spread function, an integrated spread function from among the plurality of integrated point spread functions that corresponds to a wavelength of light emitted from an illumination unit that illuminates a subject.

7. The processing apparatus according to claim 6, wherein the processor is configured to select, as the integrated spread function, an integrated point spread function from among the plurality of integrated point spread functions that corresponds to a drive pattern for driving at least one of a focus lens and an imaging element during an exposure period.

8. The processing apparatus according to claim 7, wherein the drive pattern causes a drive speed to change during the exposure period.

9. The processing apparatus according to claim 6, wherein the processor is configured to generate an image obtained by restoring an endoscopic image captured by an endoscope by the integration point spread function.

10. An endoscope comprising:
    an imaging optical system;
    an imaging element that has a two-dimensional pixel array;
    a drive unit that is capable of driving at least one of a focus lens included in the imaging optical system and the imaging element during an exposure period of the imaging element;
    an illumination unit that emits light having at least one wavelength so as to illuminate a subject; and
    a processor comprising hardware,
    wherein the processor is configured to:
       select an integrated point spread function that is used for image generation from among a plurality of integrated point spread functions; and
       generate an image using the selected integrated point spread function, and
    wherein the processor is configured to select, as the selected integrated point spread function, an integrated point spread function from among the plurality of integrated point spread functions that corresponds to the wavelength of the light emitted from the illumination unit.

11. The endoscope according to claim 10, wherein the drive unit is capable of driving at least one of the focus lens and the imaging element in a drive pattern that causes a drive speed to change during the exposure period of the imaging element.

* * * * *